United States Patent
Grega et al.

(10) Patent No.: US 6,410,760 B1
(45) Date of Patent: Jun. 25, 2002

(54) PROCESS TO PREPARE ANDROST-4-EN-17-CARBOXYLIC ACID

(75) Inventors: Kevin C. Grega, Marcellus; Scott W. Ashford, Kalamazoo, both of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/678,702

(22) Filed: Oct. 2, 2000

Related U.S. Application Data

(60) Provisional application No. 60/159,272, filed on Oct. 13, 1999.

(51) Int. Cl.$^7$ .................................................. C07J 3/00
(52) U.S. Cl. .................................................. 552/611
(58) Field of Search ........................................ 552/611

(56) References Cited

U.S. PATENT DOCUMENTS

| | | | | |
|---|---|---|---|---|
| 5,399,711 A | * | 3/1995 | Takahashi et al. | 548/453 |
| 5,405,978 A | * | 4/1995 | Herrinton | 549/544 |
| 5,478,957 A | | 12/1995 | Godard et al. | 552/610 |
| 5,481,032 A | * | 1/1996 | Pfirmann | 562/418 |
| 5,556,965 A | | 9/1996 | Godard et al. | 540/87 |
| 5,650,526 A | | 7/1997 | Roussel et al. | 552/611 |
| 5,770,748 A | * | 6/1998 | Roussel et al. | 552/531 |

FOREIGN PATENT DOCUMENTS

| WO | WO 90/00515 | 1/1990 | ........... B66C/23/70 |
|---|---|---|---|

OTHER PUBLICATIONS

J. Am. Chem.Soc., 82, 1709 (1960).
J.Org. Chem., 50, 1544 (1985).
Syn. Lett., 6, 517–518 (1996).
Tet. Lett., 36(3) 833 (1995).

Moehrle, Hans et al: "Triphenyltetrazolium chloride reaction of .alpha.–ketol steroids. Il Deoxycorticosterone" XP002159321.
Sciaky, Roberto et al: "Action of Vilsmeier reagent on oxo steroids and their derivatives. II. 20–Ketals" XP002159320.
* cited by examiner

*Primary Examiner*—Barbara P. Badio
(74) *Attorney, Agent, or Firm*—Bruce Stein

(57) ABSTRACT

The process of the present invention transforms a steroidal ketone of formula (III)

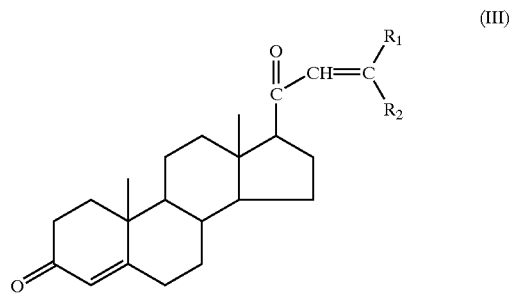

to androst-4-en-17β-carboxylic acid (IV)

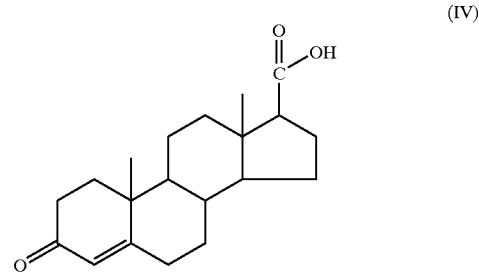

by reaction with $K_2SO_5 \cdot KHSO_4 \cdot K_2SO_4$.

18 Claims, No Drawings

PROCESS TO PREPARE ANDROST-4-EN-17-CARBOXYLIC ACID

CROSS-REFERENCE TO RELATED APPLICATIONS

This application claims the benefit of U.S. Ser. No. 60/159,272, filed Oct. 13, 1999, under 35 USC 119(e)(i).

BACKGROUND OF THE INVENTION

1. Field of the Invention

The process of the present invention is a new way to produce androst-4-en-17-carboxylic acid.

2. Description of the Related Art

*J. Am. Chem. Soc.*, 82, 1709 (1960) discloses the monoethoxalylprogesterone or 21-methoxylalylprogesterone (III).

*Tet. Lett.*, 36(3) 833 (1995) and *J. Org. Chem.*, 50, 1544 (1985) discloses that oxone is a known oxidizing agent. This and other documents discussing oxone's oxidizing properties teaches that oxone oxidation stops at the epoxide or diol stage and it does not cleave double bonds producing carboxylic acids. This includes oxidation of aldehydes to acids, amines to N-oxides, thioethers to sulfoxides or sulfones, alkenes to epoxides, cyclic ketones to lactams. There is no disclosure of the conversion of oxylates to acids.

International Publication WO90/00515 discloses the oxidation of 21-benzylidenepregn-4-ene-3,20-dione with ozone to give a seco steroid, 3,5-secoandrost-5-one-3,17β-dioic acid. The process of the present invention does not use ozone.

SUMMARY OF INVENTION

Disclosed is a process for the production of 17β-carboxyandrost-4-en-3-one (IV) or anion thereof, which comprises contacting a steroidal ketone (III) where $R_1$ is selected from the group consisting of:
(1) —OH,
(2) —$OR_{1-1}$ where $R_{1-1}$ is:
  (a) $C_1$-$C_6$ alkyl,
  (b) trimethylsilyl,
  (c) —$CH_2$-$\phi$,
where $R_2$ is selected from the group consisting of:
(1) —H,
(2) —$OR_{2-1}$ where $R_{2-1}$ is:
  (a) $C_1$-$C_6$ alkyl,
  (b) trimethylsilyl,
  (c) $\phi$-,
  (d) —$CH_2$-$\phi$,
(3) —OH,
(4) $C_1$-$C_{12}$ alkyl,
(5) $C_3$-$C_7$ cycloalkyl,
(6) —CO—$OR_{2-3}$ where $R_{2-3}$ is:
  (a) $C_1$-$C_6$ alkyl,
  (b) $C_3$-$C_7$ cycloalkyl,
  (c) -$\phi$,
(7) —CO—$NHR_{2-3}$ where $R_{2-3}$ is as defined above,
(8) —CO—$NR_{2-4}R_{2-5}$ where $R_{2-4}$ and $R_{2-5}$ are the same or different and are $C_1$-$C_6$ alkyl,
(9) -$\phi$ optionally substituted with 1 or 2 —F, —Cl, —Br, —$CH_3$, —$NH_2$, —$NO_2$, —OH, —$OCH_3$,
(10) $C_3$-$C_7$ cycloalkyl,
(11) $C_1$-$C_{12}$ alkyl with $K_2SO_5$.$KHSO_4$.$K_2SO_4$.

DETAILED DESCRIPTION OF THE INVENTION

The starting material for the process of the present invention is progesterone (I). The $C_3$-ketone of progesterone (I) must be protected as is well known to those skilled in the art. It is preferred to protect the $C_3$-ketone of progesterone (I) as an enol ether giving the $C_3$-protected progesterone (II). The preferred enol ether is the methyl or ethyl enol ether; more preferred is the methyl enol ether.

The $C_3$-protected progesterone (II) is then coverted to the corresponding steroidal ketone (i). The steroidal ketone (RD) can be of a number of different types depending on the nature of $R_1$ and $R_2$. For example, when Ris —OH and $R_2$ is:

—CO—$OR_{2-3}$, the steroidal ketone (III) is the acid derivative

STEROID-CO—$CH_2$—CO—$COOR_{2-3}$ (IIIa)

alkyl, the steroidal ketone (III) is the ketone

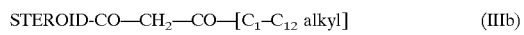

STEROID-CO—$CH_2$—CO—[$C_1$-$C_{12}$ alkyl] (IIIb)

—H, the steroidal ketone (III) is the aldehyde

STEROID-CO—$CH_2$—CO—H (IIIc)

-$\phi$, the steroidal ketone (III) is the phenyl derivative

STEROID-CO—$CH_2$—CO-$\phi$ (IIId)

—$OR_{2-1}$, the steroidal ketone (III) is the ester

STEROID-CO—$CH_2$—CO—$OR_{2-1}$ (IIIe)

It is readily apparent to those skilled in the art that the steroidal ketone (III) derivatives have corresponding tautomeric forms (III-t)

STEROID-CO—CH=C(OH)—$COOR_{2-3}$ (IIIa-t)

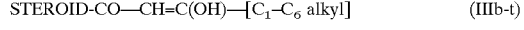

STEROID-CO—CH=C(OH)—[$C_1$-$C_6$ alkyl] (IIIb-t)

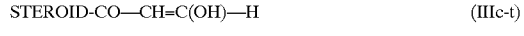

STEROID-CO—CH=C(OH)—H (IIIc-t)

STEROID-CO—CH=C(OH)-$\phi$ (IIId-t)

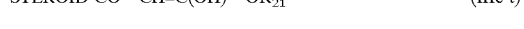

STEROID-CO—CH=C(OH)—$OR_{21}$ (IIIe-t)

The conversion of the $C_3$-protected progesterone (II) to the steroidal ketone form (III), and corresponding tautomer form (III-t) is performed my methods well known to those skilled in the art. For example if it is desired to prepare the acid derivative (IIIa), the $C_3$-protected progesterone (II) is contacted with a dialkyl oxylate and a basic system such as 25% methoxide/methanol in toluene followed by treatment with an acid such as hydrochloric acid. In fact, the preferred steroidal ketone, monoethoxalylprogesterone or 21-methoxylalylprogesterone (D) is known, see *J. Am. Chem. Soc.*, 82, 1709 (1960).

The process of the present invention is performed by contacting the steroidal ketone (III), or tautomer thereof (III-t) with OXONE. OXONE is a trademark of the DuPont Company and refers to $K_2SO_5$.$KHSO_4$.$K_2SO_4$; also known as potassium peroxymonosulfate also know as Karo's salt. The process of the present invention can be performed without any base but it is preferred to perform the process of the present invention in the presence of a weak base. The base may be either organic or inorganic. It is important that the base produce a mixture which has a pH of from about 1 to about 10; it is more preferred that the pH of the reaction mixture be from about 4 to about 9; more preferably from about 6 to about 8. Operable weak bases include bases selected from the group consisting of bicarbonate, carbonate, acetate, hydroxide, phosphate, pyridine, pyrrolidine, piperidine, piperazine, N,N-dimethylpiperazine, morpholine, N-methylmorpholine, N-methylpiperidine, dimethylaminopyridine, aniline and trialkylamines where the alkyl portion are the same or different and are $C_1$–$C_4$, It is preferred that the weak base is bicarbonate, carbonate, acetate and phosphate; it is more preferred that the weak base be aqueous bicarbonate. Operable solvents include water, ethyl acetate, ether, DMF, methylene chloride, THF, $C_1$–$C_4$ methanol, ethanol, propanol, butanol, acetonitrile, acetone, methylisobutylketone, methyl-t-butyl ether and mixtures thereof; it is preferred that the solvent is water, acetonitrile and acetone. The process of the present invention proceeds between about –30° and about 60°; it is preferred that the reaction temperature be between about 0° and about 25°.

When the reaction is determined to be complete as determined by HPLC or TLC with regard to the steroidal ketone starting material (III or III-t), the solids are removed from the crude reaction mixture (preferably by filtration) and the waste cake is rinsed with solvent (preferably acetone). The filtrate is tested for peroxide with starch/iodide paper and quenched as necessary with sodium bisulfite. The pH of the mixture should be adjusted to a pH between 4 and 5 with strong acid (preferably sulfuric acid) and worked-up as is known to those skilled in the art to provide the desired product.

The product, 17β-carboxyandrost-4-en-3-one (II) also known as oxoetiocholenic acid, 3-oxo-4-etienic acid, androst-4-ene-17-carboxylic acid or 3-oxo-4-androstene-17-β-carboxylic acid, is known see, U.S. Pat. No. 5,650,526 and *Syn. Lett.*, 6, 517–518 (1996).

DEFINITIONS

The definitions and explanations below are for the terms as used throughout this entire document including both the specification and the claims.

DEFINITIONS

All temperatures are in degrees Centigrade.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (d) downfield from TMS.

NMR refers to nuclear (proton) magnetic resonance spectroscopy, chemical shifts are reported in ppm (d) downfield from tetramethylsilane.

THF refers to tetrahydrofuran.

DMSO refers to dimethylsulfoxide.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

Oxone is a trademark of the DuPont Company and refers to $K_2SO_5 \cdot KHSO_4 \cdot K_2SO_4$; also known as potassium peroxymonosulfate also known as Karo's salt.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques and stoichiometries.

Preparation 1

21-Methoxyalylprogesterone (IIIa-t)

3-hydroxypregna-3,5-dien-20-one 3-methyl ether (II, progesterone 3-methylenol ether, 10 g) is dissolved in toluene (40 ml). Diethylglyoxylate ($C_2H_5$—O—CO—CO—O—$C_2H_5$, 5,75 g, 5.40 ml) is added followed by sodium methoxide (25%, 13.9 ml). The reaction mixture is heated to 35° and monitored by TLC. When the reaction is complete (about 3 hr), it is quenched with hydrochloric acid (10.9 ml). The reaction mixture is slowly stirred overnight and worked up the next morning by removing the lower aqueous phase, extracting with water until the pH is >2.5 and displacing the toluene with methanol. The mixture is cooled to 0–5° and filtered. The cake is washed with methanol/water (15/, 2×20 ml) and dried on a nitrogen press overnight to give the title compound, ESI MS [M–H]⁻ calculated $C_{24}H_{31}O_5$=399, found 399.

Example 1

17β-carboxyandrost-4-en-3-one (IV)

A vigorously stirred mixture of 21-Methoxyalylprogesterone (IIIa-t, PREPARATION 1, 4.0 g, 10.0 mmol) and solid sodium bicarbonate (8.40 g, 100 mmol) in acetone (100 mL) is cooled to 0–5°. A mixture of oxone (15.4 g, 25.0 mmol) in water (60 mL) is added to the slurry of 21-methoxyalylprogesterone (IIIa-t) over 15 min and the mixture is warmed to 20–25°. When the reaction is complete, the solids are removed from the crude reaction mixture by filtration and the waste cake is rinsed with acetone (50 mL). The filtrate is assayed for peroxide with starch/iodide paper and quenched as necessary with sodium thiosulfate. The pH of the mixture is adjusted to between pH 4 and 5 with sulfuric acid (1 N). the acetone is then removed under reduced pressure. The product is collected by filtration, rinsed with water and dried under a stream of nitrogen to give crude product (II).

The crude product is recrystallized by dissolving it in a solution of methanol/water/THF (80/20/10) at reflux and concentrating. The slurry is cooled to 0–5° and the solids are collected by filtration, washed with acetone/methanol (10/90) and dried under nitrogen to give the title compound; MNR (DMSO, d6, 500 MHz) 0.66, 0.87–0.93, 1.04–1.12, 1.13,1.48–1.57 (1H, m), 1.48–1.57 (2H, m), 1.58–1.73, 1.75–1.81, 1.92–2.00 (2H, m), 1.92–2.00 (2H, m), 1.92–2.00

(2H, m), 2.00–2.29, 2.34–2.43 (2H, m), 2.34–2.43 (2H, m), 5.62 and 11.89 δ; CMR (DMSO-d6, 125.77 MHz) 13.08, 16.83, 20.40, 23.17, 23.96, 31.59, 31.92, 33.56, 35.00, 35.11, 37.55, 38.14, 42.98, 53.12, 54.41, 54.62, 123.13, 170.75, 174.75, 174.55 and 197.87 δ.

CHART A

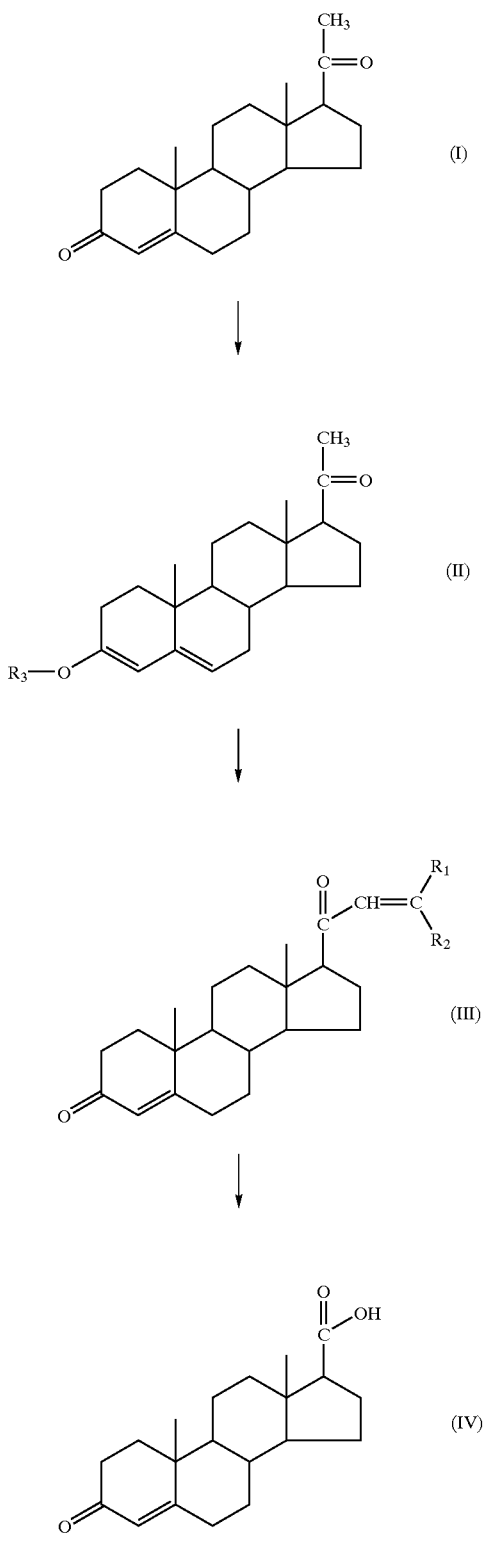

What is claimed is:

1. A process for the production of 17β-carboxyandrost-4-en-3-one (IV) or anion thereof,

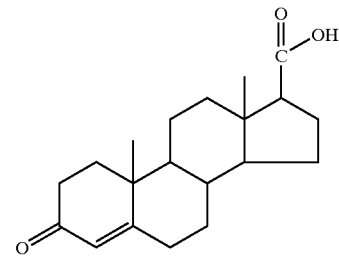

which comprises contacting a steroidal ketone (III)

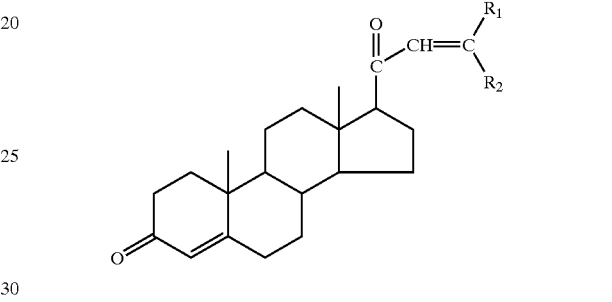

where $R_1$ is selected from the group consisting of:
—OH,
—$OR_{1-1}$ where $R_{1-1}$ is:
$C_1$–$C_6$ alkyl,
trimethylsilyl,
—$CH_2$—$C_6H_5$,
where $R_2$ is selected from the group consisting of:
—H,
—$OR_{2-1}$ where $R_{2-1}$ is:
$C_1$–$C_6$ alkyl,
trimethylsilyl,
—$C_6H_5$,
—$CH_2$—$C_6H_5$,
—OH,
$C_1$–$C_{12}$ alkyl,
$C_3$–$C_7$ cycloalkyl,
—CO—$OR_{2-3}$ where $R_{2-3}$ is:
$C_1$–$C_6$ alkyl,
$C_3$–$C_7$ cycloalkyl,
—$C_6H_5$,
—CO—$NHR_{2-3}$ where $R_{2-3}$ is as defined above,
—CO—$NR_{2-4}R_{2-5}$ where $R_{2-4}$ and $R_{2-5}$ are the same or different and are $C_1$–$C_6$ alkyl,
-phenyl optionally substituted with 1 or 2 —F, —Cl, —Br, —$CH_3$, —$NH_2$, —$NO_2$, —OH, —$OCH_3$,
$C_3$–$C_7$ cycloalkyl,
$C_1$–$C_{12}$ alkyl, with $K_2SO_5 \cdot KHSO_4 \cdot K_2SO_4$.

2. A process for the production of 17β-carboxyandrost-4-en-3-one (IV) according to claim 1 where $R_1$ is —OH.

3. A process for the production of 17β-carboxyandrost-4-en-3-one (IV) according to claim 1 where $R_2$ is —CO—$OR_{2-3}$.

4. A process for the production of 17β-carboxyandrost-4-en-3-one (IV) according to claim 3 where $R_{2-3}$ is $C_1$–$C_6$ alkyl.

5. A process for the production of 17β-carboxyandrost-4-en-3-one (IV) according to claim 4 where $R_{2-3}$ is $C_1$–$C_4$ alkyl.

6. A process for the production of 17β-carboxyandrost-4-en-3-one (IV) according to claim 5 where $R_{2-3}$ is $C_1$ or $C_2$ alkyl.

7. A process for the production of 17β-carboxyandrost-4-en-3-one (IV) according to claim 1 where the process is performed in the presence of a weak base.

8. A process for the production of 17β-carboxyandrost-4-en-3-one (IV) according to claim 7 where the weak base produces a pH of from about 1 to about 10.

9. A process for the production of 17β-carboxyandrost-4-en-3-one (IV) according to claim 8 where the weak base produces a pH of from about 4 to about 9.

10. A process for the production of 17β-carboxyandrost-4-en-3-one (IV) according to claim 7 where the weak base is selected from the group consisting of bicarbonate, carbonate, acetate, hydroxide, phosphate, pyridine, pyrrolidine, piperidine, piperazine, N,N-dimethylpiperazine, morpholine, N-methylmorpholine, N-methylpiperidine, dimethylaminopyridine, aniline and tri-alkylamines where the alkyl portion are the same or different and are $C_1$–$C_4$.

11. A process for the production of 17β-carboxyandrost-4-en-3-one (IV) according to claim 10 where the weak base is bicarbonate, carbonate, acetate and phosphate.

12. A process for the production of 17β-carboxyandrost-4-en-3-one (IV) according to claim 11 where the weak base is aqueous bicarbonate.

13. A process for the production of 17β-carboxyandrost-4-en-3-one (IV) according to claim 1 where the process is performed in a temperature range of about −30° C. to about 60° C.

14. A process for the production of 17β-carboxyandrost-4-en-3-one (IV) according to claim 13 where the process is performed in a temperature range of about 0° C. to about 25° C.

15. A process for the production of 17β-carboxyandrost-4-en-3-one (IV) according to claim 1 where the solvent is water, ethyl acetate, ether, DMF, methylene chloride, THF, methanol, ethanol, propanol, butanol, acetonitrile, acetone, methylisobutylketone, methyl-t-butyl ether and mixtures thereof.

16. A process for the production of 17β-carboxyandrost-4-en-3-one (IV) according to claim 15 where the solvent is water, acetonitrile and acetone.

17. A process for the production of 17β-carboxyandrost-4-en-3-one (IV) according to claim 1 where about 2 to about 10 equivalents of $K_2SO_5.KHSO_4.K_2SO_4$ are used.

18. A process for the production of 17β-carboxyandrost-4-en-3-one (IV) according to claim 14 where about 3 to about 6 equivalents of $K_2SO_5.KHSO_4.K_2SO_4$ are used.

* * * * *